United States Patent [19]

Fortunko

[11] 4,290,017
[45] Sep. 15, 1981

[54] APPARATUS AND METHOD FOR NONDESTRUCTIVE EVALUATION OF SURFACE FLAWS IN CONDUCTIVE MATERIALS

[75] Inventor: Christopher M. Fortunko, Thousand Oaks, Calif.

[73] Assignee: Rockwell International Corporation, El Segundo, Calif.

[21] Appl. No.: 973,295

[22] Filed: Dec. 26, 1978

[51] Int. Cl.³ ............... G01N 27/82; G01R 33/12; G01N 22/02
[52] U.S. Cl. .................. 324/237; 324/234; 331/65; 331/96; 331/107 DP; 331/117 D
[58] Field of Search ............ 324/236, 237, 238, 239, 324/240, 228, 234, 233; 331/65, 96, 107 DP, 117 D

[56] References Cited

U.S. PATENT DOCUMENTS

| | | | |
|---|---|---|---|
| 2,415,789 | 2/1947 | Farrow | 324/226 |
| 3,495,166 | 2/1970 | Lorenzi et al. | 324/228 |
| 3,909,746 | 9/1975 | Abraham et al. | 331/96 |
| 3,931,571 | 1/1976 | Hacking et al. | 324/236 |

OTHER PUBLICATIONS

Auld et al, "Methods for the Detection and Characterization of Surface in Materials", pp. 267-270, Special Report APRA/AFML Contract F33615-74-65180, 7/1/76-6/30/77.
B. Auld "Theory of Ferromagnetic Resonance Probes for Surface Cracks in Metals", G. L. Report No. 2839 Jul. 1978, Stanford Univ., Stanford Calif.

*Primary Examiner*—Gerard R. Strecker
*Assistant Examiner*—Walter E. Snow
*Attorney, Agent, or Firm*—H. Fredrick Hamann; Craig O. Malin; John J. Deinken

[57] ABSTRACT

An apparatus for characterizing a surface anomaly in an electrically conductive sample includes an oscillator with an amplifier for supplying gain to the oscillator, a feedback loop linking the input and output of the amplifier, a two port ferromagnetic resonator connected within the loop to modulate the level and frequency of oscillation of the oscillator in response to eddy currents induced in the surface of the sample by the resonator, a variable attenuator connected within the loop to adjust the power level of the oscillator, and an adjustable phase shifter connected within the loop for changing the total phase shift of the loop. A sensing circuit is operably connected to the output of the amplifier to monitor the resonance parameters of the oscillator.

17 Claims, 1 Drawing Figure

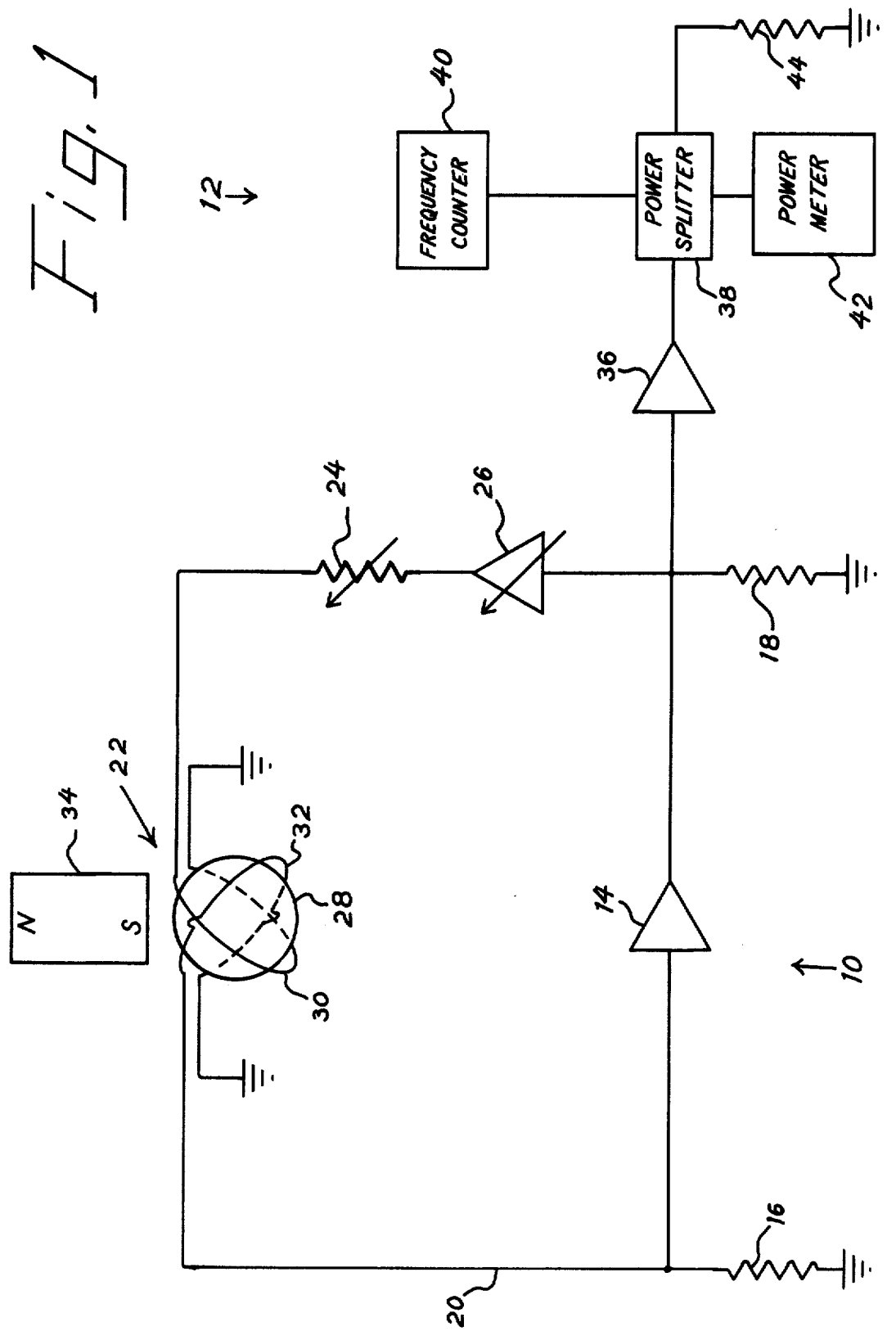

APPARATUS AND METHOD FOR NONDESTRUCTIVE EVALUATION OF SURFACE FLAWS IN CONDUCTIVE MATERIALS

STATEMENT OF GOVERNMENT INTEREST

The invention herein described was made in the course of or under a contract or subcontract thereunder, (or grant) with The Department of the Air Force.

BACKGROUND OF THE INVENTION

This invention relates to nondestructive testing and particularly to the nondestructive testing of a conductive material by utilizing microwaves to generate eddy currents in the material.

Nondestructive testing methods exhibit distinct advantages over other evaluation methods. Since the object to be tested is not destroyed, for example, an entire inventory may be tested to achieve a zero defect level. Furthermore, cleanup operations following nondestructive testing are usually minimal, such testing may frequently be done in the field, etc.

In nondestructive test methods utilizing the eddy current inspection technique, a search coil is used to generate an eddy current distribution within the electrically conducting part to be tested. The electromagnetic field generated by such eddy currents affects the electrical and magnetic characteristics of the coil, and these changes may be measured and used to determine the condition of the part.

Typical eddy current inspection systems have been restricted to the relatively low frequency portion of the electromagnetic spectrum, the frequencies generated in such systems ranging from approximately 2 KHz to 2 MHz. Ferrite cores may be employed in the prior art search coils to concentrate the flux to improve spatial resolution, and frequencies above 1 MHz may be used where the detection of small surface flaws is necessary, so that the depth of penetration (skin depth) is reduced and the interaction of the eddy currents with surface flaws is increased. In spite of these refinements, however, the ultimate detection capability of conventional coils is limited by considerations of physical size and frequency capacity. Further development of such coils appears to be hampered by the difficulty of fabricating very small search coils and by the unavailability of ferrite materials which will achieve adequate flux concentrations with high permeability at high frequencies.

An alternative approach to high frequency eddy current testing has been made feasible by substituting a ferromagnetic resonator for the standard search coil. Such a crystal will resonate when placed in a static magnetic field and subjected to a changing electromagnetic field at microwave frequencies due to electron spin procession. Ferromagnetic probes are inherently more compact than conventional high frequency eddy current probes and, in addition, have a potentially high sensitivity due to the high Q of the resonance phenomenon.

Conventional eddy current measurements are typically performed by sensing the input impedance of the search coil. In an analogous manner, a ferromagnetic resonator is connected in the reflecting mode and changes in its reflection coefficient are measured at resonance. It would be useful, however, to independently measure the real and imaginary parts of the impedance, so that both the phase shift and the change in magnitude of the impedance due to a flaw might be detected. These quantities are separately useful in the characterization of flaws in the material. Single port resonator probes, however, are not amenable to accurate phase measurement since such a probe must be operated in the reflecting mode and thus absorbs a maximum amount of energy at resonance.

Therefore, a need has developed in the eddy current nondestructive testing field for an apparatus and method which will permit the measurement of changes in both the magnitude and phase of a signal in a ferromagnetic resonant circuit at microwave frequencies.

SUMMARY OF THE INVENTION

It is a general object of this invention to provide a new and improved apparatus and method for performing nondestructive testing utilizing microwave induced eddy currents.

In one embodiment, an apparatus for detecting a surface anomaly in an electrically conductive sample according to this invention includes a two-port ferromagnetic probe for generating a first electromagnetic field, thereby inducing eddy currents within the surface of the sample, and an oscillating circuit, including the probe operably connected to the circuit in a transmission mode, adapted to respond to a second electromagnetic field generated by the eddy currents, the response of the circuit indicating the condition of the surface of the sample.

In a more particular embodiment, the probe comprises a ferromagnetic crystal, an output loop encircling the crystal, an input loop encircling the crystal and oriented orthogonal to the output loop, and a magnet adapted to produce a static magnetic field directed parallel to the planes of the input and output loops.

The magnet, which may be either a permanent magnet or an electromagnet, may be made adjustable to vary the intensity of the static magnetic field, thereby enabling the resonant frequency of the circuit to be varied.

In another more particular embodiment, the oscillating circuit includes an amplifier for providing the circuit with sufficient gain to oscillate, a feedback loop linking the input and output of the amplifier, the probe being operably connected in the feedback loop to modulate the level and frequency of resonance of the circuit, a control device operably connected in the feedback loop for adjusting the resonance parameters of the circuit, and a damping resistance connected to the circuit to load the circuit.

The apparatus may additionally include an indicator operably connected to the oscillating circuit to monitor the resonance parameters of the circuit. In a preferred embodiment, the indicator includes a buffer amplifier for isolating the indicator from the oscillating circuit, a power splitter operably connected to the buffer amplifier to divide the amplified signal, a frequency counter receiving the signal from the splitter for measuring the resonant frequency of the oscillating circuit, and a power meter receiving the signal from the splitter for measuring the power level of the oscillation.

A method for characterizing a surface anomaly in an electrically conductive sample, according to one embodiment of this invention, includes the steps of:
(a) generating eddy currents within the surface of the sample by applying a microwave signal to the sample in the presence of a static magnetic field, (b) utilizing the electromagnetic field generated by the eddy currents to modulate the power level and frequency of an oscillating circuit through a ferromagnetic resonator coupled to the oscillator in the transmission mode, (c) measuring the power level and frequency of oscillation of the oscillator, and (d) correlating the measured values to standard values to identify an anomaly within the surface of the sample.

A method for characterizing a surface anomaly in an electrically conductive sample, according to another embodiment of the invention, includes the steps of:

(a) coupling a two port ferromagnetic resonator into the feedback loop of an oscillator, (b) driving the resonator at microwave frequencies to generate eddy currents within the surface of the sample, the eddy currents in turn generating an electromagnetic field, (c) modulating the power level and frequency of oscillation of the oscillator in accordance with the effect of the eddy current-induced electromagnetic field on the resonator, (d) adjusting the attenuation and the phase shift of the feedback loop to restore the oscillation to that observed in the absence of a flaw, and (e) correlating the attenuation and phase adjustments required for a flawed sample to those for a non-flawed sample to determine the dimensions of an anomaly within the surface of the flawed sample.

Examples of the more important features of this invention have thus been broadly outlined in order that the detailed description which follows may be better understood, and so that the contributions which this invention provides to the art may be better appreciated. There are, of course, additional features of the invention which will be described herein and which are included within the subject matter of the claims appended hereto.

BRIEF DESCRIPTION OF THE DRAWING

Additional objects, features and advantages of the present invention will become apparent by referring to the following detailed description of the preferred embodiment in connection with the accompanying drawing.

In the drawing: FIG. 1 is a schematic diagram illustrating an apparatus for detecting a surface anomaly in an electrically conductive sample, according to the present invention.

DESCRIPTION OF THE PREFERRED EMBODIMENT

Now referring to FIG. 1, the preferred embodiment of a nondestructive testing apparatus constructed according to the present invention is schematically illustrated. The apparatus includes an oscillator 10 and sensing electronics 12. When the apparatus is placed in close proximity to a conductive test sample, such as a metallic part, the oscillator 10 will sense a flaw or defect in the sample, and the sensing electronics 12 will detect changes in the operating characteristics of the oscillator which, in turn, may be analyzed to determine the presence, size, and shape of such a flaw or defect.

The traditional approach to eddy current testing utilizes a small search coil to induce eddy currents in the conductive object being examined. Flaws are detected by observing changes in the input impedance of the search coil or by observing the frequency shift of a resonant circuit including the coil.

Eddy current inspections of metal parts for the presence of flaws were initially restricted to utilizing the relatively low frequency portion of the electromagnetic spectrum, typically in the frequency range from 2 KHz to 2 MHz. In specialized applications directed toward the detection of very small surface flaws, however, the use of higher frequencies is desirable in order to reduce the depth of penetration (the skin depth) of the induced eddy currents in the object being tested, thereby concentrating the reaction to the eddy currents in the region near the surface of the material.

The need for such higher frequencies has led to the use of ferromagnetic resonators in testing for surface flaws. A ferromagnetic resonator includes a ferromagnetic crystal which is positioned in a DC magnetic bias field and excited with a microwave signal through a single coupling loop. A single turn loop is sufficient to provide good coupling to the resonance, since ferromagnetic crystals exhibit a very high magnetic permeability and "Q". The resonance of the crystal occurs due to a uniform precession of the magnetic dipole moment in the crystal about the DC magnetic bias field. The principal resonant frequency is controlled by the magnitude of the DC field and, for a typical crystal of yttrium-iron-garnet (a "YIG" crystal), is above 1630 MHz. Operation at lower frequencies is possible with a gallium-doped YIG crystal, although with a concomitant sacrifice in the natural linewidth of the resonance.

The key advantages obtained by using ferromagnetic resonators in eddy current testing are that such resonators are inherently more compact than conventional high frequency eddy current probes and that the sensitivity of the ferromagnetic resonator can potentially be enhanced by the high Q of the resonance phenomena (typically 1000–2000 at 2000 MHz). Spherical YIG resonators are readily available in sizes ranging from 0.010 inch to 0.100 inch and can be operated at center frequencies ranging from 500 MHz to several tens of GHz. Moreover, because ferromagnetic resonators may be made very compact in size, the inspection of metal parts having complicated or intricate surface geometries (e.g., turbine discs, compressor parts, fasteners, etc.) is made feasible by using such equipment.

A general theory for describing the effect of a surface flaw on the operation of a ferromagnetic resonator utilizes the Lorentz reciprocity relation in the form applicable to gyromagnetic media:

$$\nabla(H_1 \times \hat{E}_2 - H_2 \times \hat{E}_1) = 0 \qquad (1)$$

where subscripts 1 and 2 indicate two solutions to the field equations and the carat indicates that the magnetic bias field is reversed. This relation is integrated over the volume enclosed by a surface around the test piece, a surface enclosing the resonator, and a closure surface at infinity. By appropriate manipulations, the change in resonator frequency and Q due to a flaw may thus be seen to be:

$$\frac{\delta \omega_o}{\omega_o} - \frac{i \delta Q_o}{2 Q_o^2} = S_F - \int \frac{\mu_o \phi_1 (\partial \hat{\phi}_2 / \partial n) dS}{2V} \qquad (2)$$

where $S_F$ is the surface opening of the flaw, potentials 1 and 2 are defined in the absence and presence of the flaw, respectively, the carat indicates a reversed bias field, and V is the stored energy in the resonator. A more complete derivation of this relationship may be found in B. A. Auld, "Theory of Ferromagnetic Resonance Probes of Surface Cracks in Metals", C. L. Report #2839, Ginzton Laboratory, Stanford University, July, 1978, which is incorporated herein by reference.

In the prior art ferromagnetic resonator testing designs, the resonator has been connected to operate in the reflection mode. Test measurements are made by electronically sweeping the input frequency to the coupling loop over the range of interest, and the RF power reflected by the resonator is detected and displayed. In this technique, the center of resonance coincides with the maximum absorption of power by the resonator. As a consequence, the center frequency of the resonance cannot be measured precisely, and it is difficult to measure separately the magnitude and phase of the impedance of the resonator, which separate measurements are desirable in order to obtain maximum information about the size and shape of surface flaws in the tested material.

It is an outstanding feature of this invention to provide an apparatus with which the magnitude and phase of the impedance can be separately measured. This result is accomplished by providing a ferromagnetic resonator which is coupled into the feedback network of an oscillator in the transmission mode. In this configuration, the resonator is used to control the frequency and the level of oscillation, which can be related to changes in the magnitude and phase of the impedance at resonance, since the conditions for oscillation are that the phase shift from the output to the input of the loop be $2\pi$ radians and that sufficient gain be present to maintain steady state oscillations. A ferromagnetic resonator can control both parameters because, if two orthogonally oriented loops are used to couple into and out of the resonator, the electrical phase shift through the resonator will be $\pi/2$ at the center of resonance. At the same time, the transmission coefficient through the resonator is maximized, as opposed to operation in the reflection mode, where the reflection coefficient is minimized at resonance.

The transmission coefficient at resonance is:

$$T(\omega_o) = \frac{4\beta^2}{Q_o 2\pi \Delta f/\omega_o} \quad (3)$$

where $\beta$ is the coupling coefficient, $Q_o$ is the unloaded Q of the resonator, $\Delta f$ is the half-power bandwidth of the loaded resonator, and $\omega_o$ is the angular frequency at resonance. Experiments have determined that both the resonant frequency and the bandwidth are affected by the presence of flaws in conductive test specimens.

Now referring to FIG. 1 in more detail, a preferred embodiment of an apparatus for implementing this approach is illustrated. The oscillator 10 includes an amplifier 14, damping resistors 16 and 18, and a feedback loop 20, which includes a YIG resonator 22, a variable attenuator 24, and a phase shifter 26.

The amplifier 14 supplies sufficient gain to the oscillator to achieve oscillation, while the damping resistors 16 and 18 are provided to load the circuit. The YIG resonator 22 is coupled to the feedback loop 20 to modulate the level and frequency of the oscillation.

Resonator 22, which is schematically illustrated in FIG. 1, includes a spherical YIG crystal 28, an input loop 30, an output loop 32, and a magnet 34. Each of loops 30 and 32 is a single turn conductor, the loops being physically arranged so that their respective planes are orthogonal. The magnet 34, which may be either a permanent magnet or an electromagnet, is physically positioned in the resonator structure so that the static magnetic field produced by the magnet is directed parallel to both the plane of loop 30 and the plane of loop 32.

The attenuator 24 may be adjusted to vary the power level of the signal within the feedback loop 20, while the phase shifter 26 enables the phase of the feedback signal to be adjusted.

Referring now to the sensing circuit 12, included in this circuit are a buffer amplifier 36, a power splitter 38, a frequency counter 40, a power meter 42, and a damping resistor 44. The buffer amplifier 36 serves to isolate the oscillator 10 from the effects of the sensing circuit 12 and provides amplification for the signal from the oscillator 10 which is supplied to the power splitter 38. Power splitter 38 divides the incoming signals equally, supplying the signal to the frequency counter 40 and the power meter 42. The frequency counter 40 provides an indication of the frequency of oscillation in the oscillator 10, while the power meter 42 indicates the power level of the oscillation.

To use the apparatus for surface flaw detection, the resonator 22 is placed close to the surface of the material to be tested and oriented so that the direction of the static magnetic field provided by the magnet 34 is normal to the surface. The resonator 22 is first placed over an area of the material known to be free of defects, and the frequency and power level are observed at resonance, with the aid of the frequency counter 40 and the power meter 42.

When the resonator is placed over a surface area containing a flaw, the effect of the flaw on the eddy currents induced in the surface of the material will cause a change in the transmission coefficient of the resonator 22. When this occurs, the phase shifter 26 is adjusted to restore the frequency of oscillation to that present in the absence of a flaw, and the attenuator 24 is adjusted to restore the power level within the oscillator to the level observed for a flawless area. Using the amounts of phase and power level adjustment required, the changes in magnitude and phase of the resonator impedance may be calculated. From these quantities, experimentally or mathematically derived relationships may be utilized to characterize the flaw which is present in the material.

Although a typical embodiment of the present invention has been illustrated and discussed herein, numerous modifications and alternative embodiments of the apparatus and method of this invention will be apparent to those skilled in the art in view of this description. Other measurement techniques, for example, could be used with the circuit illustrated, such as incorporating a gain control circuit on the amplifier 14 in place of the attenuator 24. Accordingly, this description is to be construed as illustrative only and is provided for the purpose of teaching those skilled in the art the manner of constructing the apparatus and performing the method of the invention. It is to be understood that the form of the invention shown and described herein is to be considered the presently preferred embodiment. Various changes may be made in the configuration, size, and arrangement of the parts of the invention, as will be recognized by those skilled in the art, without departing from the scope of the invention. For example, equivalent elements might be substituted for those illustrated and described herein, parts or connections might be reversed or otherwise interchanged, and certain features of the invention might be utilized independently of the use of other features, all as will be apparent to one skilled in the art after receiving the benefit attained through reading the foregoing description of the invention.

What is claimed is:

1. An apparatus for detecting a surface anomaly in an electrically conductive sample, comprising:
   a two port ferromagnetic crystal probe, including an input port and an output port; and
   an oscillating circuit, including a feedback loop, said ferromagnetic probe being coupled to said loop in a transmission mode through said input and output ports, whereby the precession resonance of the crystal thereby controls the frequency and level of oscillation of said oscillation circuit and eddy currents induced in the surface of the sample by the probe modulate the level and frequency of oscillation in response to a surface anomaly.

2. The apparatus of claim 1, wherein said probe comprises a ferromagnetic resonator.

3. The apparatus of claim 2, wherein said resonator comprises:
   a ferromagnetic crystal;
   an output loop encircling said crystal;
   an input loop encircling said crystal and oriented orthogonal to said output loop; and
   a magnet adapted to produce a static magnetic field directed parallel to the planes of said input and output loops.

4. The apparatus of claim 3, wherein said crystal comprises an yttrium-iron-garnet crystal.

5. The apparatus of claim 3, wherein said magnet is adjustable to vary the intensity of said static magnetic field, thereby affording adjustment of the resonant frequency of said circuit.

6. The apparatus of claim 3, wherein said magnet comprises a permanent magnet.

7. The apparatus of claim 3, wherein said magnet comprises an electromagnet.

8. The apparatus of claim 1, wherein said oscillating circuit comprises:
   an amplifier for providing said circuit with sufficient gain to oscillate;
   a feedback loop linking the input and output of said amplifier, said probe being operably connected in said feedback loop to modulate the level and frequency of resonance of said circuit;
   a control device operably connected in said feedback loop for adjusting the resonance parameters of said circuit; and
   a damping resistance connected to said circuit to load said circuit.

9. The apparatus of claim 8, wherein said control device further comprises:
   an adjustable attenuator for varying the power level of said circuit; and
   an adjustable phase shifter for changing the phase of said feedback loop.

10. The apparatus of claim 1, further comprising an indicator operably connected to said oscillating circuit for monitoring the resonance parameters of said circuit.

11. The apparatus of claim 10, wherein said indicator further comprises:
    a frequency counter for measuring the resonant frequency of said oscillating circuit; and
    a power meter for measuring the level of oscillation in said oscillating circuit.

12. The apparatus of claim 11, wherein said indicator further comprises:
    a buffer amplifier for isolating said indicator from said oscillating circuit; and
    a power splitter operably connected to said buffer amplifier to divide the signal from said oscillating circuit and supply said signal to said frequency counter and said power meter.

13. An apparatus for detecting a surface anomaly in an electrically conductive sample, comprising:
    an oscillator, including an amplifier for supplying gain to said oscillator and a feedback loop linking the input and output of said amplifier;
    a two port ferromagnetic resonator, including an input port and an output port, coupled to said loop in a transmission mode through said input and output ports;
    a variable attenuator connected within said loop to adjust the power level of said oscillator;
    an adjustable phase shifter connected within said loop for changing the total phase shift of said loop; and
    a sensing circuit operably connected to the output of said amplifier to monitor the resonance parameters of said oscillator.

14. The apparatus of claim 13, wherein said resonator further comprises:
    a ferromagnetic crystal;
    an input loop encircling said crystal and connected to the output of said amplifier;
    an output loop encircling said crystal in a plane orthogonal to the plane of said input loop and connected to the input of said amplifier; and
    a magnet adapted to produce a static magnetic field in a direction parallel to both the plane of said input loop and the plane of said output loop.

15. The apparatus of claim 14, wherein said ferromagnetic crystal is spherical.

16. A method for characterizing a surface anomaly in an electrically conductive sample, comprising the steps of:
    generating eddy currents within the surface of the sample by applying a microwave signal to the sample in the presence of a static magnetic field;
    utilizing the electromagnetic field generated by the eddy currents to modulate the power level and frequency of an oscillating circuit through a ferromagnetic resonator coupled to the oscillator in the transmission mode;
    measuring the power level and frequency of oscillation; and
    correlating the measured values to standard values to identify an anomaly within the surface of the sample.

17. A method for characterizing a surface anomaly in an electrically conductive sample, comprising the steps of:
    coupling a two port ferromagnetic resonator into the feedback loop of an oscillator;
    driving the resonator at microwave frequencies to generate eddy currents within the surface of the sample, the eddy currents in turn generating an electromagnetic field;
    modulating the power level and frequency of oscillation of the oscillator in accordance with the effect of the eddy current-induced electromagnetic field on the resonator;

adjusting the attenuation and the phase shift of the feedback loop to restore the oscillation to that observed in the absence of a flaw; and correlating the attenuation and phase adjustments required for a flawed sample to those for a non-flawed sample to determine the dimensions of an anomaly within the surface of the flawed sample.

* * * * *